United States Patent
Feiweier et al.

(10) Patent No.: US 9,636,422 B2
(45) Date of Patent: May 2, 2017

(54) METHOD FOR DETECTING A BRAIN REGION WITH NEURODEGENERATIVE CHANGE

(75) Inventors: Thorsten Feiweier, Poxdorf (DE); Diana Martin, Herzogenaurach (DE); Günther Platsch, Röthenbach (DE); Sebastian Schmidt, Weisendorf (DE); Kristin Schmiedehausen, Palo Alto, CA (US); Michael Szimtenings, Bonn (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 2695 days.

(21) Appl. No.: 12/219,609

(22) Filed: Jul. 24, 2008

(65) Prior Publication Data

US 2009/0030304 A1 Jan. 29, 2009

(30) Foreign Application Priority Data

Jul. 26, 2007 (DE) .................. 10 2007 034 956

(51) Int. Cl.
*A61K 49/00* (2006.01)
*A61B 6/03* (2006.01)
(Continued)

(52) U.S. Cl.
CPC ........ *A61K 49/0004* (2013.01); *A61B 5/4064* (2013.01); *A61B 5/4088* (2013.01); *A61B 6/037* (2013.01); *A61B 6/5247* (2013.01)

(58) Field of Classification Search
USPC .......................................... 600/411; 324/318
See application file for complete search history.

(56) References Cited

U.S. PATENT DOCUMENTS 5,732,702 A * 3/1998 Mueller ................. 600/410
6,226,352 B1 * 5/2001 Salb ..................... 378/98.9
(Continued)

FOREIGN PATENT DOCUMENTS

| DE | 10 2005 015 071 | 10/2006 |
| DE | 10 2005 023 907 | 12/2006 |
| WO | WO 2006/009887 | 1/2006 |

OTHER PUBLICATIONS

Mark et al, Amyloid β-Peptide Impairs Glucose Transport in Hippocampal and Cortical Neurons: Involvement of Membrane Lipid Peroxidation, The Journal of Neuroscience, Feb. 1, 1997 17(3):1046-1054.*

(Continued)

*Primary Examiner* — Unsu Jung
(74) *Attorney, Agent, or Firm* — Harness, Dickey & Pierce PLC (57) ABSTRACT

A computerized method is disclosed for detecting a brain region with neurodegenerative change and also a brain region with vascular change in the brain of a patient and also an imaging arrangement suitable for this. In at least one embodiment, the method includes recording a first data record of the brain via positron emission tomography and a second data record of the brain via magnetic resonance imaging; reconstructing a PET image from the first data record and an MRI image from the second data record; identifying evidence for a brain region with vascular change in the MRI image; segmenting the MRI image into gray matter and white matter; identifying a brain region with neurodegenerative change in the PET image; and superposing the PET image and the segmented MRI image to determine whether the brain region with neurodegenerative change is present in gray matter or in white matter, the recording of the first data record and the second data record (Continued)

being carried out in quick succession without repositioning the patient or is even carried out simultaneously.

18 Claims, 3 Drawing Sheets

(51) Int. Cl.
*A61B 6/00* (2006.01)
*A61B 5/00* (2006.01)

(56) References Cited

U.S. PATENT DOCUMENTS

| | | |
|---|---|---|
| 6,385,479 B1 * | 5/2002 | Sibbitt et al. ............... 600/410 |
| 7,323,874 B2 | 1/2008 | Krieg et al. |
| 2005/0113667 A1 * | 5/2005 | Schlyer et al. ............ 600/411 |
| 2005/0226527 A1 * | 10/2005 | Weese et al. ............... 382/275 |
| 2006/0084858 A1 * | 4/2006 | Marks ......................... 600/407 |
| 2006/0266947 A1 | 11/2006 | Krieg et al. |

OTHER PUBLICATIONS

German Office Action issued Apr. 18, 2008.

* cited by examiner

FIG 5

METHOD FOR DETECTING A BRAIN REGION WITH NEURODEGENERATIVE CHANGE

PRIORITY STATEMENT

The present application hereby claims priority under 35 U.S.C. §119 on German patent application number DE 10 2007 034 956.6 filed Jul. 26, 2007, the entire contents of which is hereby incorporated herein by reference.

FIELD

Embodiments of the present invention generally relate to a computerized method for detecting a brain region with neurodegenerative change and also a brain region with vascular change in the brain of a patient, a corresponding computer program, a data storage medium on which the computer program is saved, and/or an imaging arrangement for carrying out the method.

BACKGROUND

Neuropathological changes such as, in particular, degenerative or vascular changes with different causes in specific brain regions cause possible dementia. A comprehensive examination of dementia which is as accurate as possible also requires imaging methods in addition to clinical, neuropsychological and laboratory tests. Magnetic resonance imaging—abbreviated MRI—and nuclear medical imaging—abbreviated NM—are usually used for this purpose. Their reliability varies depending on the type and characteristics of the dementia. For example, the onset of Alzheimer's disease can be verified in the early stages using the nuclear medical method known as positron emission-tomography—abbreviated PET. In this case, the glucose metabolism of the brain is visualized on the basis of 18-fluorodeoxyglucose (i.e. a radioactively marked glucose)—abbreviated FDG. A brain region with vascular change due to circulatory disorders often manifests itself in the so-called white matter of the brain, which can be displayed in MRI, but not as well with PET based on FDG. Depending on the illness or the stage of the illness, either MRI or PET is better; the symptoms of the two illnesses can be very similar. Often the examination is concluded after carrying out one of the two previously mentioned imaging methods, if an indication of dementia is diagnosed. A second illness present at the same time is not detected. Among the reasons for this are a high expenditure of time and limited cooperation of the respective patients. It is clear that the detection of such brain regions can only be implemented with the aid of electronic imaging and image evaluation methods and machines, that is to say generally with the aid of computers.

Since it is often the case in patients that hybrid forms of dementia are present or have to be excluded, it could often be necessary to carry out both a PET and MRI for a precise examination. Both methods require a high expenditure of time and require cooperative patients who are able to lie still on two, occasions for approximately 30 min. In the case of a patient group with the presently described illness, this is often not possible or is possible only after the administration of sedatives. The latter could in turn influence the PET. These examination procedures sometimes place an enormous strain on both the patient and the medical staff.

Previously, only one of the two examinations was carried out in the daily clinical routine, which carries the possible risk of an incomplete examination. Alternatively the two examinations were carried out with large logistical effort—differing from patient to patient—and with the aid of sedatives, if applicable. Due to the required expenditure of time, the risk of movement artifacts, and hence insufficient image quality, is increased in the case of two sequentially carried out examinations. An appropriate method for improving the image quality is described in DE 10 2005 023 907 A1.

SUMMARY

In at least one embodiment, the present invention specifies a computerized method for detecting a brain region with neurodegenerative change and a brain region with vascular change in the brain and an imaging arrangement which carries out this method, which method and arrangement are favorable with regard to the expenditure of time and with which, especially in the case of uncooperative patients, a reliable data basis for a complete examination can be provided.

Two different imaging methods are combined with one another in a single apparatus in the case of so-called hybrid modalities. An example is a combined MRI/PET machine, which permits isocentric acquisition of magnetic resonance data records and positron emission data records simultaneously or at least in quick succession.

The method according to at least one embodiment of the invention permits, after recording a first—positron emission—data record and a second—magnetic resonance—data record, a combined evaluation of these data records. For this purpose, the two data records are advantageously recorded simultaneously within a single examination cycle (often also called a session), without repositioning the patient. In this case, the PET image reconstructed from the positron emission data record primarily delivers important indications of possible Alzheimer's disease, while the MRI image reconstructed from the magnetic resonance data mainly supplies possible indications of a brain region with vascular change. Thus both types of dementia can be distinguished well, in particular in the early stages. Only in a late stage of mixed dementia does distinguishing on the basis of a magnetic resonance data record and a positron emission data record become rather blurred.

Segmenting the two data records allows examination as to whether correspondingly changed brain regions are present. This examination is only carried out if, for example, a specific accumulation or depletion of the radioactively marked marker in the changed brain region can be observed by means of the positron emission data record. As a result, only those brain regions which can be causal for dementia are examined in the positron emission data record and magnetic resonance data record.

In addition, according to at least one embodiment of the invention, the second data record is used to improve the diagnostic significance of the PET measurement or the brain region with neurodegenerative change identified in the PET image. For this purpose, the MRI image is subdivided by segmentation into gray matter and white matter—for example into cortex and non-cortex—and the result of the segmentation is transferred to the PET image by fusion with it. In other words, the two images are superposed, and as a result it is determined whether the brain region with neurodegenerative change is located in gray matter and thus indicates Alzheimer's disease.

It should be noted that the steps of data recording and image processing and image evaluation explained above do not necessarily have to be carried out in the specified order. By way of example, identifying the various changed brain regions or segmenting the MRI image can be carried out in a different order, or at least partially in parallel.

According to a further embodiment of the method, specific radiopharmaceuticals can be administered for this purpose, such as fluoro-18-deoxyglucose and/or 2-(1-{6-[(2-[fluoro-18]ethyl)(methyl)amino]-2-naphthyl}-ethylidene) malononitrile—abbreviated F-18-FDDNP. The last-mentioned, more specific radiopharmaceutical accumulates in particular in the so-called amyloid plaques. For example, approximately spherical, clumped-together deposits of proteins outside neurons are called amyloid. Such plaques are linked to Alzheimer's disease.

On the other hand, only those segmented brain regions of the magnetic resonance data record which have been changed by vascular-dependent dementia can be examined. In particular, greatly decreased brain blood circulation can be displayed by means of perfusion MRI. For this purpose, a contrast agent can be added to the blood.

It can also be provided to stimulate a functional brain region (a brain region associated with a specific brain function) during the recording of a functional magnetic resonance data record. In this way, a causal connection between the brain region segmented by the functional magnetic resonance data record and the brain region with vascular change, for example, can be established.

An advantageous development of at least one embodiment of the method provides for the magnetic resonance data record to be used for movement correction of the positron emission information. The movement correction is particularly important for patients suffering from dementia especially, since their motor skills and the skill of lying still are adversely affected. A functional magnetic resonance data record comprising the functional brain region can also be corrected. Anatomical structures from the magnetic resonance data record can be used as a possible reference point for this purpose.

The two data records based on magnetic resonance and positron emission are recorded within one session and thus with one frame of reference. It follows that the data records are practically co-registered. This can lead to inaccuracies during the segmentation of the three-dimensional brain region of the positron emission data record. For improved segmentation of this brain region, i.e. for the actual improvement of the spatial resolution of the PET image, the method is developed in such a way that the positron emission data record is subject to a partial volume correction on the basis of the magnetic resonance data record. In the partial volume effect, the signal source—i.e. the lesion—does not correspond to the voxels of the PET image, for example only filling a fraction of a voxel, which leads to an erroneous signal.

In the method according to at least one embodiment of the invention, an image of the segmented brain regions can be generated by way of the imaging method. The image can visualize the brain region causing dementia in a clear fashion. Both the functional brain regions and anatomical structures of the brain can be integrated into the image for improved orientation. The latter are to be reconstructed from the magnetic resonance data record.

In an advantageous manner, the brain regions segmented in each case by the positron emission data record and the magnetic resonance data record are transferred to the image in different colors. The image thus contains in particular indications about mixed dementia. Also, the absence of color information could lead to conclusions as to the presence of only vascular dementia or dementia only due to amyloid depositions or not vascular. In addition, due to a now markedly reduced examination time, a precise investigation of the effects of various medicines on brain regions with different neuropathological changes can be carried out. This additionally allows more cost-effective development of new medicines by the pharmaceutical industry.

The imaging arrangement according to at least one embodiment of the invention for detecting a brain region with neurodegenerative change and also a brain region with vascular change in the brain of a patient comprises:
  a positron emission tomography imaging apparatus for recording a first data record of the brain,
  a magnetic resonance imaging apparatus for recording a second data record of the brain and for displaying an MRI image reconstructed therefrom,
  a display apparatus for displaying a PET image reconstructed from the first data record having a brain region with neurodegenerative change and/or displaying an MRI image reconstructed from the second data record having a brain region with vascular change and/or displaying an image created by superposition of the PET image having a brain region with neurodegenerative change and the MRI image segmented into gray matter and white matter, and
  a control and evaluation system for controlling the imaging arrangement.

The method according to at least one embodiment of the invention can be carried out efficiently and easily using such an imaging arrangement.

BRIEF DESCRIPTION OF THE DRAWINGS

Example embodiments of the present invention are now described in more detail with reference to the attached drawings, in which

FIGS. 4*a,b* show two images of segmented brain regions according to a further example embodiment of the method.

In the following text, the example embodiments of the present invention are described with reference to the drawings.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Figure 1:
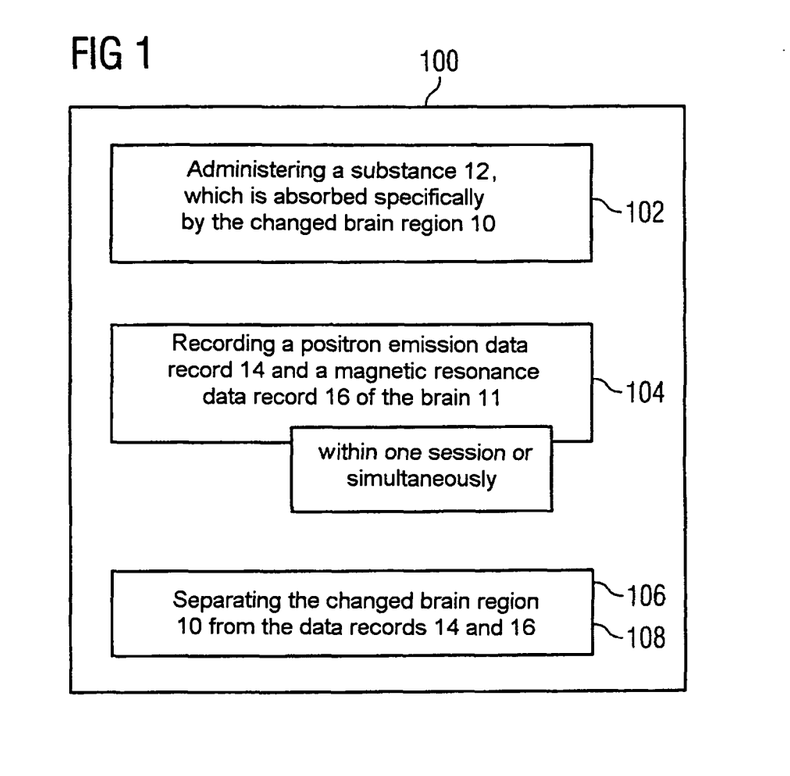
FIG. 1 shows a schematic illustration of a first example embodiment of a method according to the invention.

FIG. 1 shows the individual steps of a method 100 for detecting a brain region 10 with neurodegenerative change and a brain region 13 with vascular change. In a first step 102, a radioactively marked substance 12 is administered to a-person to be examined, that is to say a patient. This substance 12 is in this case absorbed specifically by the brain region 10 changed by neurodegenerative dementia. This specificity can manifest itself as both above and below average concentration in the changed brain region 10 with reference to unchanged tissue. Fluorine-18 is used as the positron-emitting isotope. In this exemplary embodiment, correspondingly marked 2-(1-{6-[(2-[fluoro-18]ethyl)(methyl)amino]-2-naphthyl}-ethylidene)malononitrile is used as the substance 12. This substance 12 is absorbed by so-called amyloid plaques in an increased concentration and is detected in a further method step 104 by means of positron emission tomography. In addition to a first—positron emission—data record 14 of the brain 11, a second—magnetic resonance—data record 16 is also recorded. To decrease the measuring time required for this, according to the invention it is provided to simultaneously carry out the recording 104 of the two data records 14 and 16. In addition to substantial saving of time, an increased utilization of machines, such as a so-called BrainPET, with integrated positron emission functionality and magnetic resonance functionality is achieved. Here, the recording 104 of the data records 14 and 16 in one frame of reference is achieved automatically, which alternatively is also possible at different times within one session without repositioning the patient. In this case, the data records 14 and 16 are co-registered. In particular, this saves further work during further processing.

The further processing provides for segmenting the reconstructed PET image to localize a changed brain region 10 in the positron emission data record 14 in method step 106. In this case, the segmentation supplies important indications for dementia in certain brain regions 10 on the basis of biochemistry. If such a changed brain region 10 is not present, no data material is extracted from the positron emission data record 14 and put to further use for creating an image 20.

An MRI image is reconstructed from the magnetic resonance data record 16 and a brain region 13, changed due to vascular dementia, is, if present, identified therefrom preferably by segmentation. Such changed brain regions 13 can be recognized as vascular lesions in the white (or gray) brain matter in a T2-weighted MRI or in a so-called FLAIR-MRI. As a supplement, decreased circulation of the changed brain region 13 can be illustrated by means of perfusion MRI. This magnetic resonance data record 16 permits the identification or determination of stenoses, which, inter alia, decrease rest perfusion in the changed brain region 13. These brain regions 13 with decreased circulation due to vessel constrictions are illustrated in reconstructions of the magnetic resonance data record 16 in the form of a different grayscale value.

Furthermore, according to an embodiment of the invention, the second data record 16 is used to improve the diagnostic significance of the PET measurement or brain region 10 with neurodegenerative change identified in the PET image. For this purpose, the MRI image is subdivided by way of segmentation into gray matter and white matter (in this exemplary embodiment into cortex and non-cortex) and the segmentation result is transferred onto the PET image by means of fusion with the latter. The two images are thus superposed, and, as a result, it is determined whether the brain region 10 with neurodegenerative change is located in gray matter and thus indicates Alzheimer's disease.

In addition to saving time, it is possible to record the entire brain 11. A reliable data basis is created by means of the method according to an embodiment of the invention in order to track the type and extent of dementia in the case of complex psychological findings. An aid for examining and distinguishing neurodegenerative dementia and vascular dementia is specified.

Figure 2:
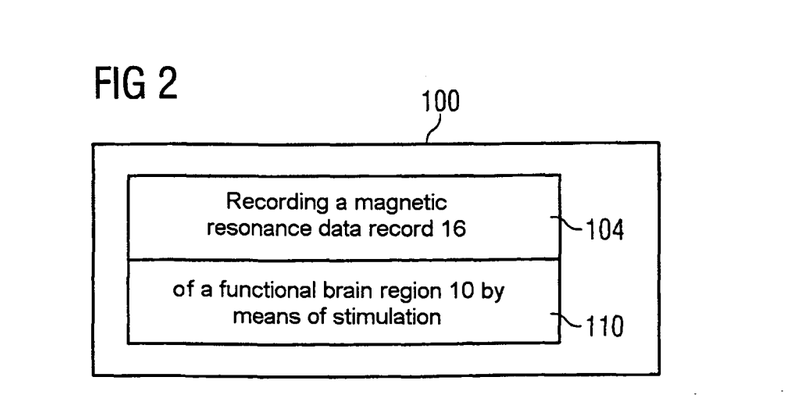
FIG. 2 shows a partial view according to a second example embodiment of the present invention.

In a second example embodiment of the method 100 according to the invention, as shown in FIG. 2, a functional brain region 10 is stimulated during the recording of a functional magnetic resonance data record 18. By way of example, this stimulation 110 is carried out by a patient with a speech impediment suspected to be caused by dementia being requested to talk during the recording 104. By these devices/methods, the speech center can be segmented using the recorded magnetic resonance data record 16. If the segmented brain regions 10 of the positron emission data record 14 and/or the magnetic resonance data record 16 are now superposed with the speech center, this can be an important indication. This superposition can be readily determined since the two data records 14 and 16 are recorded by means of isocentrically arranged detectors.

Figure 3:
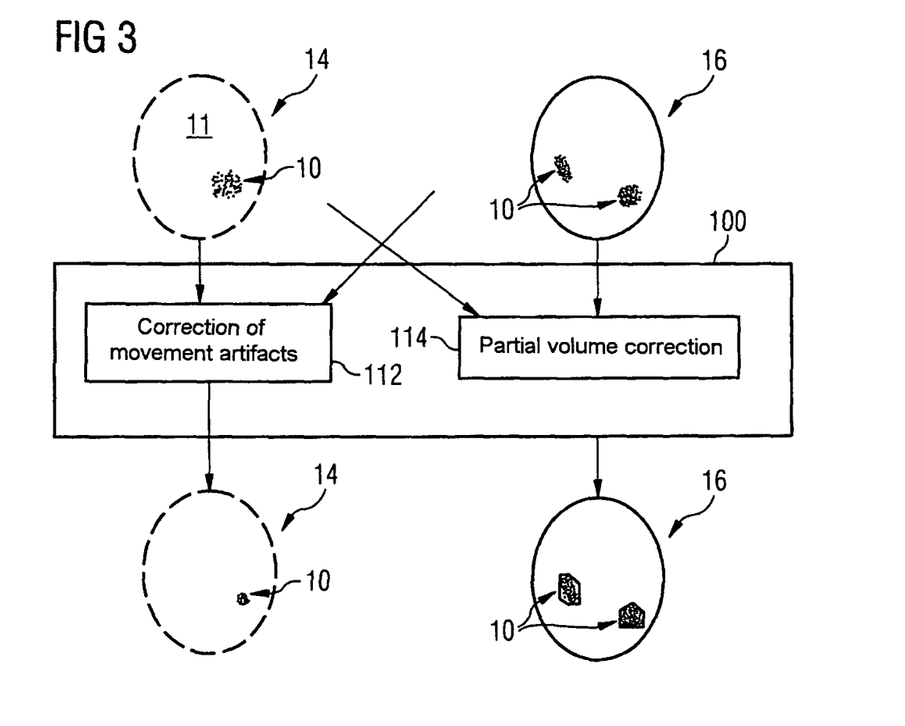
FIG. 3 shows a part of a method according to the invention for correcting data records of a brain on the basis of a third example embodiment.

The recording 104 of the positron emission data record 14 is carried out by way of gamma detectors, which record gamma radiation created in a so-called annihilation process during the combination of a positron with an electron. By way of example, in order to be able to segment an amyloid plaque region in the positron emission data record 14, a recording time of approximately 30 minutes is required. A reconstruction of a positron emission data record 14 is shown top left in FIG. 3. A discontinuous circumferential line of the brain 11 is determined as an orientation aid from the reconstruction of the magnetic resonance data record 16 shown top right.

Brain regions 10 or 13 (not illustrated in this case) with neuropathological change are determined from the two data records 14 and 16. Due to the relatively long recording time, the brain region 10 shown on the left has an increased spatial extent due to movement artifacts. These movement artifacts are corrected by means of the magnetic resonance data record 16 recorded with a markedly higher temporal resolution. For this purpose, a local spatial displacement of the positron emission data record 14 over the recording time is determined by the magnetic resonance data record 16, and the determined points of the data record 14 are adapted. The results of this correction 112 are shown bottom left in FIG. 3. There is therefore no need to seduce the patient.

When recording the magnetic resonance data record 16, a functional brain region 10 is stimulated, with a functional magnetic resonance data record 18 being obtained. Movement artifacts likewise occur in this case, as shown top right in FIG. 3, which can be removed by a correction 112 based on a magnetic resonance data record 16.

A further correction 114 with reference to the positron emission data record 14 is to be carried out by way of the magnetic resonance data record 16. This relates to three-dimensional segmentation of the changed brain region 10. The magnetic resonance data record 16 is recorded as a three-dimensional data record which has an improved resolution of the brain region 10 in all three spatial dimensions. A peculiarity of the positron emission data record 14 known as the partial volume effect is corrected in this process. The three-dimensional extent of the brain region 10 of the positron emission data record 14 is segmented, as shown bottom left in FIG. 3.

Figure 4:
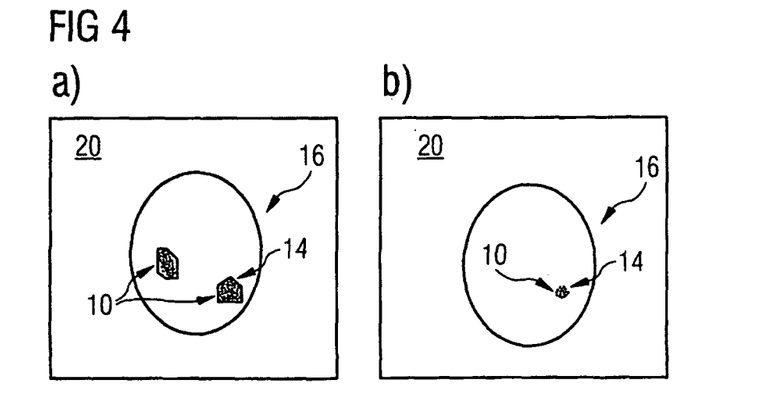

As already described above, only brain regions 10 or 13 with neuropathological change are determined by the two data records 14 and 16 by segmentation. According to a further example embodiment of the method 100 according to the invention, an image 20 is generated from the brain regions 10 and 13 segmented in this way. FIG. 4a shows a combined image 20 of the reconstructions of the two data records 14 and 16 illustrated at the bottom of FIG. 3.

As opposed to the image 20 shown in FIG. 4b, the changed brain regions 10 are segmented by the two data records 14 and 16. This is an important indication of so-called mixed dementia. The right image 20 shows in addition to the circumferential line only a brain region 10 segmented by the positron emission data record 14. Due to the very clear visualization it can be assumed that during the recording 104 of data records 14 and 16 only dementia known as Alzheimer's disease was present.

In FIG. 4a the respectively segmented brain regions 10 or 13 having different shapes are visualized. The brain region 10 segmented by the positron emission data record 14 is illustrated as a hexagon. The brain region 13 segmented by the magnetic resonance data record 16 is illustrated as a pentagon. The brain region 10 illustrated bottom right has a superposition which can easily be recognized due to the different illustrations of the segmented data records 14 and 16 which indicates mixed dementia.

By way of the method according to an embodiment of the invention, it is possible to obtain important indications for detecting mixed dementia, vascular dementia and/or dementia on the basis of Alzheimer's disease by way of an examination. Likewise, this data acquired simultaneously can be used for diagnosis or differential diagnosis of other forms of dementia. Reliably distinguishing between deviations of an anatomical brain structure—so-called normal variants—which change the positron emission data record and actual dementia is also possible. The disclosed method is thus significantly faster than two examinations carried out sequentially. Both magnetic resonance imaging and positron emission tomography can be carried out by means of so-called MRI/PET hybrid systems. The advantages of the two methods are hence meaningfully combined and permit a comprehensive and precise diagnosis. This permits both improved therapy planning and more robust prognosis estimations. This faster and more reliable method has a greater potential for the introduction and testing of new medicines.

Anatomical and functional changes can be displayed simultaneously on the basis of the magnetic resonance data record. The combination with the positron emission data record permits the examination of biochemical changes in the brain. The resultant decreased examination time additionally increases patient comfort and decreases the amount of sedative to be administered and the strain on the medical staff. A combined application gives the user a significant competitive edge since, in particular, the first-class MRI/PET hybrid systems can be utilized in an improved fashion.

Figure 5:
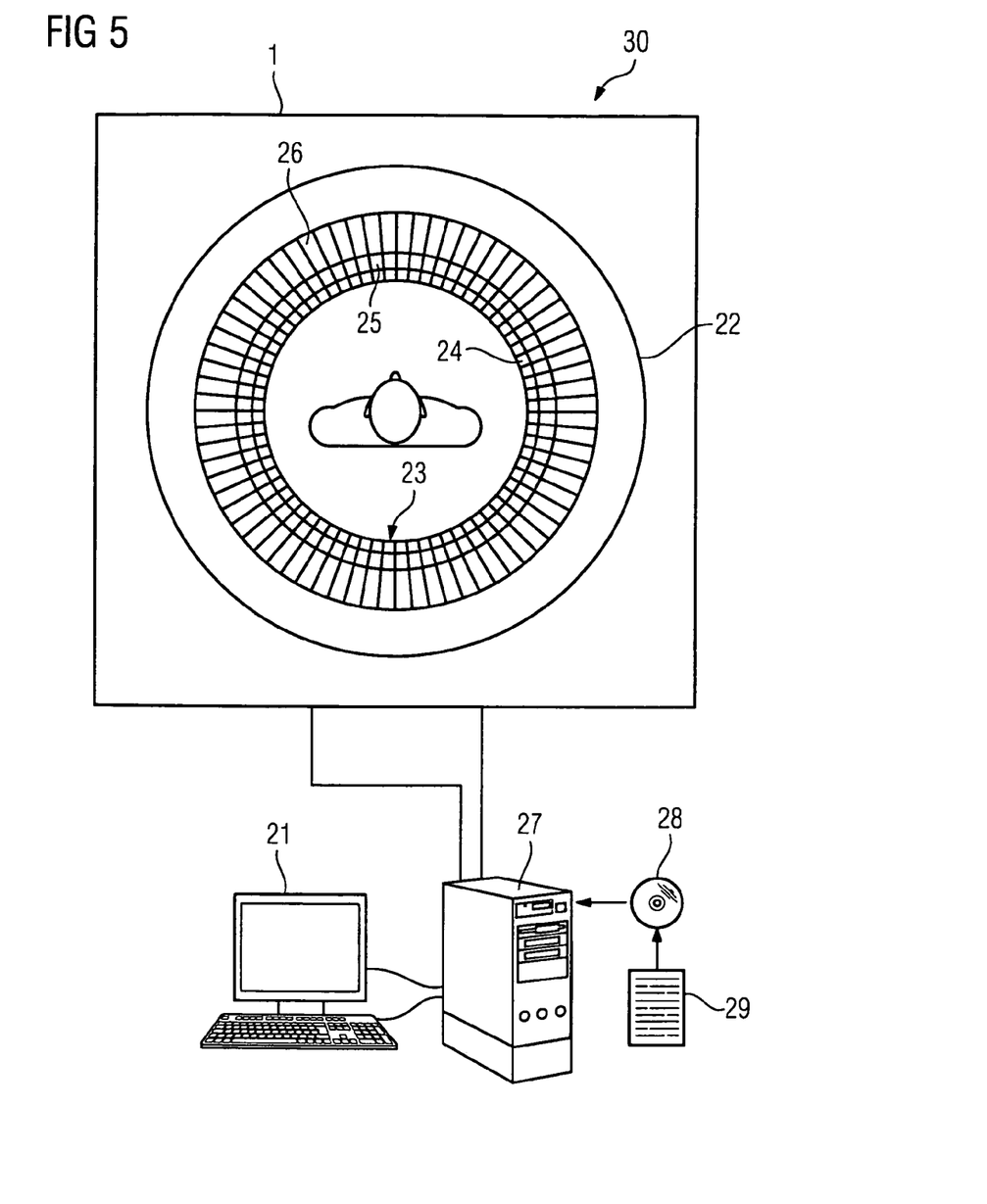
FIG. 5 shows a cross-sectional view of an imaging arrangement according to an example embodiment of the invention that is not to scale.

FIG. 5 schematically shows an imaging arrangement 30 according to an embodiment of the invention. It includes a generally known MRI tube 22 for recording an MRI data record 16 of the brain 11 of a patient. A plurality of mutually opposing PET detection units 23 arranged in pairs are arranged coaxially within the MRI tube 22 around the longitudinal direction for recording a PET data record 14 of the brain 11. The PET detection units 23 preferably include a photodiode array 25 with an upstream array of crystals 24 and an electric amplifying circuit (PMT) 26. However, the invention is not limited to PET detection units 23 with the photodiode array 25 and the upstream array of crystals 24; instead differently designed photodiodes, crystals and apparatuses can similarly be used for detection.

The MRI tube 22 defines a cylindrical, first measurement field along its longitudinal direction. The plurality of PET detection units 23 define a cylindrical, second measurement field along the longitudinal direction. Preferably, the second measurement field of the PET detection units 23 substantially corresponds to the first measurement field of the MRI tube 22. For example, this is implemented by a corresponding adaptation of the arrangement density of the PET detection-units 23 along the longitudinal direction.

The image acquisition and image processing is carried out under the control of a computer or processor 27, operated on the basis of a program 29 (symbolically illustrated-as a written page) which, by way of example, is saved on a CD as a data storage medium 28. The images generated by the imaging arrangement 30 can be displayed on a monitor 21.

Using the imaging arrangement 30 according to an embodiment of the invention and the method according to an embodiment of the invention, both a brain region 10 with neurodegenerative change and a brain region 13 with vascular change in the brain 11 of a patient can be reliably acquired automatically, i.e. computer-based, without having to worry that, in the presence of two such differently changed brain regions 10, 13, only one is acquired and the other is overlooked.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROM's and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computerized method for detecting a brain region with neurodegenerative change and also a brain-region with vascular change in the brain of a patient, the computerized method comprising:
   recording a positron emission data record of the brain via positron emission tomography and a magnetic resonance data record of the brain via magnetic resonance imaging, the recording of the positron emission data record and the magnetic resonance data record being carried out one of in succession without repositioning the patient, or simultaneously;
   reconstructing a PET image from the positron emission data record and an MRI image from the magnetic resonance data record;
   identifying evidence for a brain region with vascular change in the MRI image;
   segmenting the MRI image into gray matter and white matter;
   identifying a brain region with neurodegenerative change in the PET image; and
   superposing, in response to observing a changed brain region in the PET image, the PET image and the segmented MRI image to determine whether the identified brain region with neurodegenerative change is present in gray matter or in white matter.

2. The method as claimed in claim 1, wherein a functional brain region is stimulated during the recording of a functional magnetic resonance data record.

3. The method as claimed in claim 2, wherein a correction of movement artifacts in the positron emission data record is carried out based on the magnetic resonance data record.

4. The method as claimed in claim 2, wherein the positron emission data record is subject to a partial volume correction based on the magnetic resonance data record.

5. The method as claimed in claim 2, wherein an image of the brain region with neurodegenerative change and of the brain region with vascular change is generated.

6. The method as claimed in claim 2, wherein the brain region with neurodegenerative change and the brain region with vascular change are transferred to the image in different colors.

7. The method as claimed in claim 6, further comprising:
   administering a radioactively marked substance, absorbed specifically by the brain region, with neurodegenerative change.

8. The method as claimed in claim 7, wherein the substance used is fluoro-18-deoxyglucose or 2-(1-{6-[(2-[fluoro-18]ethyl)(methyl)amino]-2-naphthyl}-ethylidene) malono-nitrile.

9. The method of claim 2, wherein a correction of movement artifacts in the functional magnetic resonance data record is carried out based on the magnetic resonance data record.

10. The method as claimed in claim 1, wherein a correction of movement artifacts in the positron emission data record is carried out based on the magnetic resonance data record.

11. The method as claimed in claim 1, wherein the positron emission data record is subject to a partial volume correction based on the magnetic resonance data record.

12. The method as claimed in claim 1, wherein an image of the brain region with neurodegenerative change and of the brain region with vascular change is generated.

13. The method as claimed in claim 1, wherein the brain region with neurodegenerative change and the brain region with vascular change are transferred to the image in different colors.

14. The method as claimed in claim 13, further comprising:
   administering a radioactively marked substance, absorbed specifically by the brain region, with neurodegenerative change.

15. The method as claimed in claim 14, wherein the substance used is fluoro-18-deoxyglucose or 2-(1-{6-[(2-[fluoro-18]ethyl)(methyl)amino]-2-naphthyl}-ethylidene) malono-nitrile.

16. The method of claim 1, wherein a correction of movement artifacts in a functional magnetic resonance data record is carried out based on the magnetic resonance data record.

17. A tangible computer readable data storage medium storing computer executable instructions that, when executed, cause a control and evaluation system of an imaging arrangement to carry out the method of claim 1.

18. A non-transitory computer readable medium including program segments for, when executed on a computer device, causing the computer device to implement the method of claim 1.

* * * * *